US005378475A

United States Patent [19]

Smith et al.

[11] Patent Number: 5,378,475
[45] Date of Patent: Jan. 3, 1995

[54] SUSTAINED RELEASE DRUG DELIVERY DEVICES

[75] Inventors: Thomas J. Smith, Boston, Mass.; Paul Ashton; Paul A. Pearson, both of Lexington, Ky.

[73] Assignee: University of Kentucky Research Foundation, Lexington, Ky.

[21] Appl. No.: 658,695

[22] Filed: Feb. 21, 1991

[51] Int. Cl.$^6$ .......................... A61K 9/22; A61K 9/32
[52] U.S. Cl. .......................... 424/473; 424/422; 424/423; 424/424; 424/427; 424/468; 514/772.2; 514/912; 514/914
[58] Field of Search ............... 424/425, 426, 427, 473, 424/422, 423, 474

[56] References Cited

U.S. PATENT DOCUMENTS

| | | | |
|---|---|---|---|
| 3,416,530 | 12/1968 | Ness | 424/427 |
| 3,618,604 | 11/1971 | Ness | 604/294 |
| 3,630,200 | 12/1971 | Higuchi | 128/260 |
| 3,632,739 | 1/1972 | Kornblum | 424/465 |
| 3,896,819 | 7/1975 | Zaffaroni et al. | 128/833 |
| 3,916,899 | 11/1975 | Theeuwes et al. | 424/424 |
| 3,961,628 | 6/1976 | Arnold | 424/427 |
| 3,977,404 | 8/1976 | Theeuwes | 424/427 |
| 3,980,463 | 9/1976 | Muramoto et al. | 504/116 |
| 3,993,071 | 11/1976 | Higuchi et al. | 424/428 |
| 4,008,719 | 2/1977 | Theeuwes et al. | 424/427 |
| 4,014,334 | 3/1977 | Theeuwes et al. | 424/427 |
| 4,014,335 | 3/1977 | Arnold | 424/427 |
| 4,034,758 | 7/1977 | Theeuwes | 424/427 |
| 4,036,227 | 7/1977 | Zaffaroni et al. | 424/428 |
| 4,077,407 | 3/1978 | Theeuwes et al. | 424/427 |
| 4,111,201 | 9/1978 | Theeuwes | 424/473 |
| 4,111,203 | 9/1978 | Theeuwes | 604/892.1 |
| 4,135,514 | 1/1979 | Zaffaroni et al. | 424/528 |
| 4,142,526 | 3/1979 | Zaffaroni et al. | 424/524 |
| 4,186,184 | 1/1980 | Zaffaroni | 424/14 |
| 4,200,098 | 4/1980 | Ayer et al. | 424/424 |
| 4,247,498 | 7/1981 | Castro | 264/41 |
| 4,256,108 | 3/1981 | Theeuwes | 424/424 |
| 4,290,426 | 9/1981 | Luschen et al. | 424/428 |
| 4,326,525 | 4/1982 | Swanson et al. | 424/427 |
| 4,327,725 | 5/1982 | Cortese et al. | 424/427 |
| 4,439,196 | 3/1984 | Higuchi | 424/473 |
| 4,475,916 | 10/1984 | Himmelstein | 424/427 |
| 4,519,801 | 5/1985 | Edgren | 424/427 |
| 4,519,909 | 5/1985 | Castro | 264/41 |

(List continued on next page.)

FOREIGN PATENT DOCUMENTS 180708 6/1986 European Pat. Off. .
0316838 5/1989 European Pat. Off. .

OTHER PUBLICATIONS

Pearson et al, Proceed. Intern. Symp. Control Rel. Bioch. Mater. 17(1990) Controlled Release Society, Jul. 22-25, pp. 470, 171.
Sustained Release Drug Delivery Systems in Extracapsular Cataract Surgery, ARVO Annual Meeting (Apr. 29-May 4, 1990), Solomon et al.
Polyvinyl Alcohol Membrane Permeability Character-
(List continued on next page.)

Primary Examiner—G. S. Kishore
Assistant Examiner—James M. Spear
Attorney, Agent, or Firm—Burns, Doane, Swecker & Mathis

[57] ABSTRACT

A method and device for treating a mammalian organism to obtain a desired local or systemic physiological or pharmacological effect is provided. The method includes administering a sustained release drug delivery system to a mammalian organism in need of such treatment at an area wherein release of an effective agent is desired and allowing the effective agent to pass through the device in a controlled manner. The device includes an inner core or reservoir comprising the effective agent; a first coating layer, which is essentially impermeable to the passage of the effective agent; and a second coating layer, which is permeable to the passage of the effective agent. The first coating layer covers at least a portion of the inner core; however, at least a small portion of the inner core is not coated with the first coating layer. The second coating layer essentially completely covers the first coating layer and the uncoated portion of the inner core.

35 Claims, 3 Drawing Sheets

U.S. PATENT DOCUMENTS

| | | | |
|---|---|---|---|
| 4,522,625 | 6/1985 | Edgren | 424/473 |
| 4,609,374 | 9/1986 | Ayer | 424/473 |
| 4,615,698 | 10/1986 | Guittard et al. | 424/473 |
| 4,624,847 | 11/1986 | Ayer et al. | 424/473 |
| 4,627,850 | 12/1986 | Deters et al. | 424/452 |
| 4,652,441 | 3/1987 | Okada et al. | 424/497 |
| 4,657,543 | 4/1987 | Langer et al. | 424/486 |
| 4,673,405 | 6/1987 | Guittard et al. | 424/473 |
| 4,681,755 | 7/1987 | Columbo et al. | 424/486 |
| 4,692,336 | 9/1987 | Eckenhoff et al. | 424/468 |
| 4,693,886 | 9/1987 | Ayer | 424/473 |
| 4,711,782 | 12/1987 | Okada et al. | 424/455 |
| 4,716,031 | 12/1987 | Eckenhoff et al. | 424/453 |
| 4,717,567 | 1/1988 | Wu et al. | 424/462 |
| 4,720,384 | 1/1988 | Di Luccio et al. | 264/41 |
| 4,730,013 | 3/1988 | Bondi et al. | 424/427 |
| 4,777,049 | 10/1988 | Magruder et al. | 424/457 |
| 4,786,500 | 11/1988 | Wong | 424/422 |
| 4,832,957 | 5/1989 | Dempski et al. | 424/469 |
| 4,839,177 | 6/1989 | Columbo et al. | 424/482 |
| 4,861,627 | 8/1989 | Mathiowitz et al. | 424/462 |
| 4,877,618 | 10/1989 | Reed, Jr. | 424/448 |
| 4,889,720 | 12/1989 | Konishi | 424/447 |
| 4,891,223 | 1/1990 | Ambegaonkar et al. | 424/408 |
| 4,898,733 | 2/1990 | DePrince et al. | 424/425 |
| 4,913,906 | 4/1990 | Friedman et al. | 424/499 |
| 4,927,687 | 5/1990 | Nuwayser | 424/449 |
| 4,952,402 | 8/1990 | Sparks et al. | 424/419 |
| 4,994,273 | 2/1991 | Zentner et al. | 424/422 |
| 5,028,435 | 7/1991 | Katz et al. | 424/484 |
| 5,098,443 | 3/1992 | Parel et al. | 623/4 |
| 5,141,752 | 8/1992 | Ayer et al. | 424/473 |

OTHER PUBLICATIONS istics of 5-Fluorouracil, Journal of Ocular Pharmacology, vol. 4, No. 2 (1988), Smith et al.

Intraocular Sustained Release of ANtiviral Agents of AIDS, proceedings of the 17th International Symposium on Controlled Release of Bioactive Materials (Jul. 22-25, 1990), Smith et al.

"A Membrane Based Sustained Release Ocular Delivery System for 5-Fluorouacil", *Investigative Ophthalomology and Visual Science*, vol. 30, No. 4 (May 1989), Smith et al.

"Polyvinyl Alcohol Membrane Permeability Characteristics of Gancyclovir", *Investigative Ophthalomology and Visual Science*, vol. 30, No. 4 (May 1989), Pearson et al.

"5-Fluorouracil Sustained Release Device Implantation: Toxicology and Histology in Rabbits", vol. 31, No. 4 (May 1990), Hollins et al.

"Intravitreal Sustained Release of Gancyclovir", *Investigative Ophthalmology and Visual Science*, vol. 31, No. 4 (May 1990), Goins et al.

SUSTAINED RELEASE DRUG DELIVERY DEVICES

FIELD OF THE INVENTION

The present invention relates to a novel sustained release drug delivery device comprising an inner core or reservoir containing an agent effective in obtaining a desired local or systemic physiological or pharmacological effect, a first coating essentially impermeable to the passage of the effective agent, and a second coating permeable to the passage of the effective agent. The first coating covers at least a portion of the inner core; however, at least a small portion of the inner core is not coated with the first coating layer. The second coating layer essentially completely covers the first coating layer and the uncoated portion of the inner core. The portion of the inner core which is not coated with the first coating layer allows passage of the agent into the second coating layer thus allowing controlled release.

BACKGROUND OF THE INVENTION

Over the years, various drugs have been developed to assist in the treatment of a wide variety of ailments and diseases. However, in many instances such drugs are not capable of being administered either orally or intravenously without the risk of various detrimental side effects.

For example, intravenous ganciclovir (GCV) is effective in the treatment of CMV retinitis in AIDS patients, but bone marrow toxicity limits its usefulness. The incidence of neutropenia (absolute neutrophil count <1000) during intravenous GCV therapy ranges from 30 to 50%. Continuous maintenance GCV therapy is necessary to prevent progression or recrudescence of the disease, but despite maintenance therapy 30 to 50% of patients experience a relapse during treatment. Other problems associated with systemic GCV administration include the risk of sepsis related to permanent indwelling catheters and the inability to receive concurrent therapy with zidovudine (AZT) which has been shown to prolong life and improve the immune function in AIDS patients.

Intravitreal GCV injections of 200 to 400 μg administered once or twice weekly have resulted in temporary remission of CMV retinitis in AIDS patients. Intravitreal GCV injections may provide a higher intraocular drug concentration than systemic therapy and reduce the incidence of neutropenia. Current treatment of CMV retinitis in AIDS patients is clearly suboptimal. Ganciclovir is virustatic and thus disease inhibition requires maintenance drug administration.

Due to the risks that certain drugs impose, researchers have developed systems for administering such drugs to aid in the treatment of these ailments and diseases. Many of these systems provide a release rate which reduces the occurrence of detrimental side effects.

One such delivery device is an orally administered pill or capsule which contains a drug encapsulated within various layers of a composition that dissolves over a period of time in the digestive tract, thereby allowing a gradual or slow release of the drug into the system.

Another type of device for controlling the administration of such drugs is produced by coating a drug with a polymeric material permeable to the passage of the drug to obtain the desired effect. Such devices are particularly suitable for treating a patient at a specific local area without having to expose the patient's entire body to the drug. This is advantageous because any possible side effects of the drug could be minimized.

Such systems are particularly suitable for treating ailments affecting the eye. Advances for administering a drug to the external surface of the eye are disclosed in U.S. Pat. No. 4,014,335 to Arnold. Arnold describes various ocular inserts that act as a deposit or drug reservoir for slowly releasing a drug into the tear film for prolonged periods of time. These inserts are fabricated of a flexible polymeric material that is biologically inert, non-allergenic, and insoluble in tear fluid. To initiate the therapeutic programs of these devices, the ocular inserts are placed in the cul-de-sac between the sclera of the eyeball and the eyelid for administering the drug to the eye.

Devices formed of polymeric materials that are insoluble in tear fluid retain their shape and integrity during the course of the needed therapy to serve as a drug reservoir for continuously administering a drug to the eye and the surrounding tissues at a rate that is not effected by dissolution or erosion of the polymeric material. Upon termination of the desired therapeutic program, the device is removed from the cul-de-sac.

Another type of device used for sustained release of a drug to the external surface of the eye, described in U.S. Pat. No. 3,416,530, is manufactured with a plurality of capillary openings that communicate between the exterior of the device and the interior chamber generally defined from a polymeric membrane. While these capillary openings in this construction are effective for releasing certain drugs to the eye, they add considerable complexity to the manufacture of the device because it is difficult to control the size of these openings in large scale manufacturing using various polymers.

Another device, described in U.S. Pat. No. 3,618,604, does not involve such capillary openings, but instead provides for the release of the drug by diffusion through a polymeric membrane. The device, in a preferred embodiment, as disclosed in that patent, comprises a sealed container having the drug in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

Another such device, described in U.S. Pat. No. 4,014,335, comprises a three-layered laminant having a pair of separate and discrete first and third walls formed of a material insoluble in tear fluid with one of the walls formed of a drug release material permeable to the passage of drug and the other wall formed of a material impermeable to the passage of the drug.

The above described systems and devices are intended to provide sustained release of drugs effective in treating patients at a desired local or systemic level for obtaining certain physiological or pharmacological effects. However, there are many disadvantages associated with their use including the fact that it is often times difficult to obtain the desired release rate of the drug. The need for a better release system is especially significant in the treatment of CMV retinitis. Thus, there remains a long-felt need in the art for an improved system for providing sustained release of a drug to a patient to obtain a desired local or systemic physiological or pharmacological effect. In addition, all of these devices release their drug into the tear film. If relatively high levels are required inside the eye, such devices are essentially useless.

SUMMARY OF THE INVENTION

It is, therefore, a primary objective of the present invention to provide a device suitable for the controlled and sustained release of a composition effective in obtaining a desired local or systemic physiological or pharmacological effect.

The device, in one embodiment, includes an inner core or reservoir which contains an agent effective in obtaining the desired effect. The device further includes a first coating layer. The first coating layer is essentially impermeable to the passage of the agent and covers a portion of the inner core. The first coating layer blocks passage of the agent from the inner core at those sides where it contacts the inner core. The remaining portion of the inner core which is not blocked allows a controlled amount of the agent from the inner core to pass into the second coating layer. The second coating layer is permeable to the passage of the agent and covers essentially the entire first coating layer and the exposed inner core. The first coating layer is positioned between the inner core and the second coating layer in order to control the rate at which the agent permeates through the second coating layer.

Another object of the present invention is to provide a method for treating a mammalian organism, e.g., human, to obtain a desired local or systemic physiological or pharmacological effect. The method includes positioning the sustained released drug delivery system at an area wherein release of the agent is desired and allowing the agent to pass through the second coating to the desired area of treatment.

Another object of the present invention is to provide an ocular device suitable for direct implantation into the vitreous of the eye. Such devices of the present invention are surprisingly found to provide sustained controlled release of various compositions to treat the eye without risk of detrimental side effects.

Another object of the present invention is to provide an ocular delivery system that could be applied to an intraocular lens to prevent inflamation or posterior capsular opacification.

With the foregoing as well as other objects, advantages, features and aspects of the invention that will become hereinafter apparent, the nature of the invention may be more clearly understood by reference to the detailed description of the invention and to the appended claims.

BRIEF DESCRIPTION OF THE DRAWINGS

In the drawings, which are not drawn to scale, but are set forth to illustrate various embodiments of the invention, the figures are as follows.

DETAILED DESCRIPTION OF THE PREFERRED EMBODIMENTS OF THE INVENTION

More specifically, the present inventors have surprisingly discovered a device that is suitable for the controlled and sustained release of an agent effective in obtaining a desired local or systemic physiological or pharmacological effect.

The device includes an inner core or reservoir which contains an agent effective in obtaining a desired effect. The device further includes a first coating layer and a second coating layer. The first coating layer covers only a portion of the inner core and is impermeable to the passage of the agent. The second coating layer covers all of the inner core and the first coating layer and is permeable to the passage of the agent. The portion of the inner core that is not coated with the first coating layer facilitates passage of the agent through the second coating layer.

Specifically, the first coating layer is positioned between the inner core and the second coating layer such that it blocks the passage of the agent through the adjacent portions of the second coating layer thus controlling the rate of passage of the agent.

Figure 1:
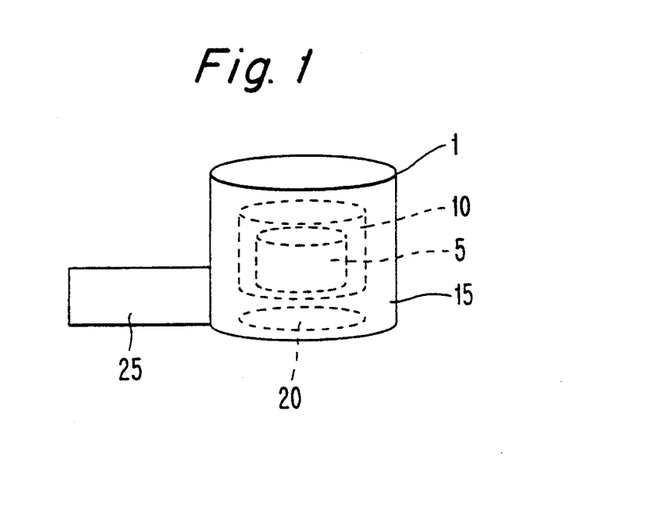
FIG. 1 is an enlarged view of one embodiment of the sustained release drug delivery device showing inner core, first coating layer and second coating layer.

FIG. 1 illustrates one embodiment of the sustained release drug delivery device of the present invention. While the device shown in FIG. 1 is cylindrical, the device could be any shape. The device comprises an inner core or reservoir 5, an impermeable coating 10 which is impermeable to the passage of the agent in the core or reservoir 5, and a permeable coating 15 which is permeable to the passage of the agent in the core or reservoir 5. FIG. 1 further shows an impermeable cap 20 and suture tag 25.

Figure 2:
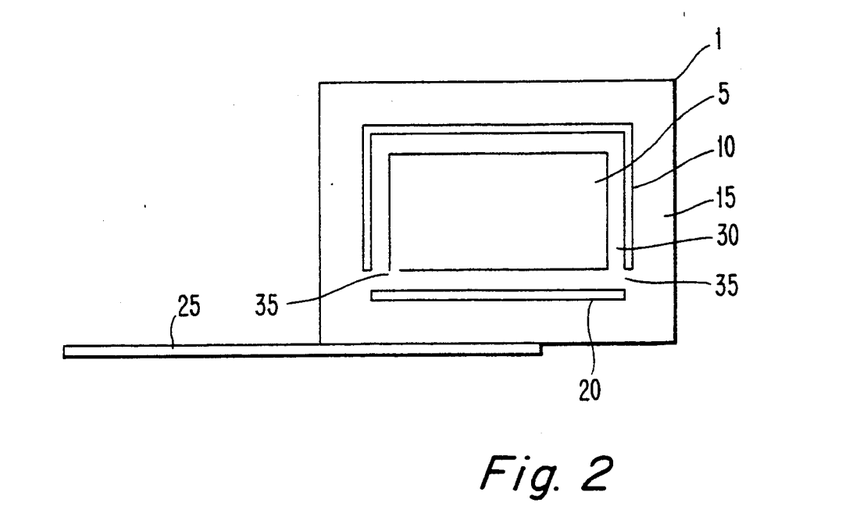
FIG. 2 is an enlarged cross sectional schematic of one embodiment of the sustained release drug delivery device showing inner core, first coating layer and second coating layer.
Figure 3:
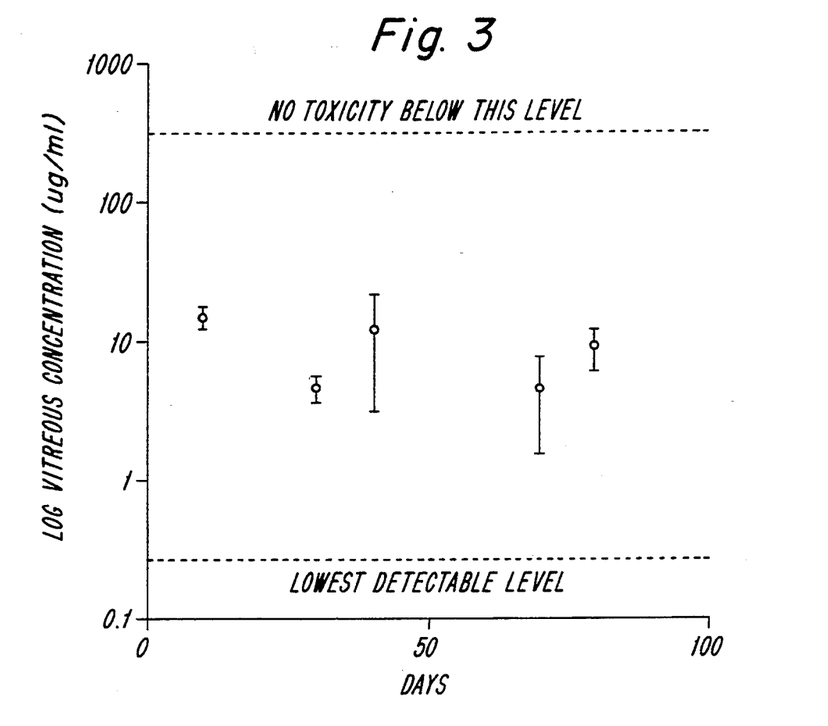
FIG. 3 is a graph showing the concentration of ganciclovir found in test rabbits and delivered by an ocular device of the present invention over time.

FIG. 2 illustrates, in cross section, the device shown in FIG. 1. As illustrated, there may be a permeable coating 30 between the core or reservoir 5 and the impermeable coating 10. The permeable coating 30 may be made of the same material as the permeable coating 15. In the embodiment illustrated in FIG. 2, the impermeable cap 20 is positioned such that there is a passage 35 which allows passage of the agent in the core or reservoir. The impermeable coating 20 is positioned between the permeable coating 15 and the reservoir or core 5. The suture tag 25 is attached to the permeable coating 15.

The invention further relates to a method for treating a mammalian organism to obtain a desired local or systemic physiological or pharmacological effect. The method includes administering the sustained release drug delivery system to the mammalian organism and allowing the agent effective in obtaining the desired local or systemic effect to pass through the second coating to contact the mammalian organism. The term administering, as used herein, means positioning, inserting, injecting, implanting, or any other means for exposing the device to a mammalian organism. The route of administration depends on a variety of factors including type of response or treatment, type of agent and preferred site of administration.

The devices in certain embodiments have applicability in providing a controlled and sustained release of agents effective in obtaining a desired local or systemic physiological or pharmacological effect relating at least to the following areas: treatment of cancerous primary tumors, (e.g., glioblastoma); chronic pain; arthritis; rheumatic conditions; hormonal deficiencies such as diabetes and dwarfism; and modification of the immune response such as in the prevention of transplant rejection and in cancer therapy. A wide variety of other disease states may also be prevented or treated using the drug delivery device of the present invention. Such disease states are known by those of ordinary skill in the art. For those not skilled in the art, reference may be made to Goodman and Gilman, The Pharmacological Basis of Therapeutics, 8th Ed., Pergamon Press, NY, 1990; and Remington's Pharmaceutical Sciences, 18th Ed., Mack Publishing Co., Easton, Pa., 1990; both of which are incorporated by reference herein.

In addition, the devices are suitable for use in treating mammalian organisms infected with AIDS and AIDS related opportunistic infections such as cytomegalovirus infections, toxoplasmosis, pneumocystis carinii and mycobacterium avium intercellular.

The devices are particularly suitable for treating ocular conditions such as glaucoma, proliferative vitreoretinopathy, diabetic retinopathy, uveitis, and keratitis. The devices are also particularly suitable for use as an ocular device in treating mammalian organisms suffering from cytomegalovirus retinitis wherein the device is surgically implanted within the vitreous of the eye.

As described above, the inner core or reservoir contains an agent effective in obtaining a desired local or systemic physiological or pharmacological effect. The following classes of agents could be incorporated into the devices of the present invention: anesthetics and pain killing agents such as lidocaine and related compounds and benzodiazepam and related compounds; anti-cancer agents such as 5-fluorouracil, adriamycin and related compounds; anti-inflammatory agents such as 6-mannose phosphate; anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antiglaucoma drugs such as beta-blockers: timolol, betaxolol atenolol, etc; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; and carbonic anhydrize inhibitors.

In addition to the above agents, other agents are suitable for administration to the eye and its surrounding tissues to produce a local or a systemic physiologic or pharmacologic beneficial effect. Examples of such agents include antibiotics such as tetracycline, chlortetracycline, bacitracin, neomycin, polymyxin, gramicidin, oxytetracycline, chloramphenicol, gentamycin, and erythromycin; antibacterial such as sulfonamides, sulfacetamide, sulfamethizole and sulfisoxazole; antivirals, including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone; decongestants such as phenylephrine, naphazoline, and tetrahydrazoline; miotics and anti-cholinesterase such as pilocarpine, eserine salicylate, carbachol, di-isopropyl fluorophosphate, phospholine iodine, and demecarium bromide; mydriatics such as afropine sulfate, cyclopentolate, homatropine, scopolamine, tropicamide, eucatropine, and hydroxyamphetamine; and sympathomimetics such as epinephrine. Once again, reference may be made to any standard pharmaceutical textbook such as Remington's Pharmaceutical Sciences for the identify of other agents.

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate and the like.

A large number of polymers can be used to construct the devices of the present invention. The only requirements are that they are inert, non-immunogenic and of the desired permeability.

Materials that may be suitable for fabricating the first or second coating layer of the device include naturally occurring or synthetic materials that are biologically compatible with body fluids and eye tissues, and essentially insoluble in body fluids with which the material will come in contact. The use of rapidly dissolving materials or materials highly soluble in eye fluids are to be avoided since dissolution of the wall would affect the constancy of the drug release, as well as the capability of the system to remain in place for a prolonged period of time.

Naturally occurring or synthetic materials that are biologically compatible with body fluids and eye tissues and essentially insoluble in body fluids which the material will come in contact include, but are not limited to, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4°-isopropylidene diphenylene carbonate), vinylidene chloride, acrylonitrile copolymer, vinyl chloride-diethyl fumerale copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

Specifically, the first layer of the device of the present invention may be made of any of the above-listed polymers or any other polymer which is biologically compatible with body fluids and eye tissues, essentially insoluble in body fluids which the material will come in contact and essentially impermeable to the passage of the effective agent. The term impermeable, as used herein, means that the layer will not allow passage of the effective agent at a rate required to obtain the desired local or systemic physiological or pharmacological effect.

The first layer must be selected to be impermeable, as described above, to the passage of the agent from the inner core out to adjacent portions of the second coating layer. The purpose is to block the passage of the agent to those portions and thus control the release of the agent out of the drug delivery device.

The composition of the first layer, e.g., the polymer, must be selected so as to allow the above-described controlled release. The preferred composition of the first layer will vary depending on such factors as the active agent, the desired rate of control and the mode of administration. The identity of the active agent is important since the size of the molecule, for instance, is critical in determining the rate of release of the agent into the second layer.

Since the first coating layer is essentially impermeable to the passage of the effective agent, only a portion of the inner core or reservoir may be coated with the first coating layer. Depending on the desired delivery rate of the device the first coating layer may coat only a small portion of the surface area of the inner core for faster release rates of the effective agent or may coat large portions of the surface area of the inner core for slower release rates of the effective agent.

For faster release rates, the first coating layer may coat up to 10% of the surface area of the inner core. Preferably, approximately 5-10% of the surface area of the inner core is coated with the first coating layer for faster release rates.

For slower release rates, the first coating layer may coat at least 10% of the surface area of the inner core. Preferably, at least 25% of the surface area of the inner core is coated with the first coating layer. For even slower release rates, at least 50% of the surface area may be coated. For even slower release rates, at least 75% of the surface area may be coated. For even slower release rates, at least 95% of the surface area may be coated.

Thus, any portion of the surface area of the inner core up to but not including 100% may be coated with the first coating layer as long as the desired rate of release of the agent is obtained.

The first coating may be positioned anywhere on the inner core, including but not limited to the top, bottom or any side of the inner core. In addition, it could be on the top and a side, or the bottom and a side, or the top and the bottom, or on opposite sides or on any combination of the top, bottom or sides.

The second layer of the device of the present invention must be biologically compatible with body fluids and eye tissues, essentially insoluble in body fluids which the material will come in contact and permeable to the passage of the agent or composition effective in obtaining the desired effect.

The effective agent diffuses in the direction of lower chemical potential, i.e., toward the exterior surface of the device. At the exterior surface of the device, equilibrium is again established. When the conditions on both sides of the second coating layer are maintained constant, a steady state flux of the effective agent will be established in accordance with Fick's Law of Diffusion. The rate of passage of the drug through the material by diffusion is generally dependent on the solubility of the drug therein, as well as on the thickness of the wall. This means that selection of appropriate materials for fabricating the wall will be dependent on the particular drug to be used.

The rate of diffusion of the effective agent through a polymeric layer of the present invention may be determined via diffusion cell studies carried out under sink conditions. In diffusion cell studies carried out under sink conditions, the concentration of drug in the receptor compartment is essentially zero when compared to the high concentration in the donor compartment. Under these conditions, the rate of drug release is given by:

$$Q/t = (D.K.A.DC)/h$$

where Q is the amount of drug released, t is time, D is the diffusion coefficient, K is the partition coefficient, A is the surface area, DC is the difference in concentration of the drug across the membrane, and h is the thickness of the membrane.

In the case where the agent diffuses through the layer via water filled pores, there is no partitioning phenomena. Thus, K can be eliminated from the equation. Under sink conditions, if release from the donor side is very slow, the value DC is essentially constant and equal to the concentration of the donor compartment. Release rate therefore becomes dependent on the surface area (A), thickness (h) and diffusivity (D) of the membrane. In the construction of the device of the present invention, the size (and therefore, surface area) is mainly dependent on the size of the effective agent.

Thus, permeability values may be obtained from the slopes of a Q versus time plot. The permeability P, can be related to the diffusion coefficient D, by:

$$P = (K.D)/h$$

Once the permeability is established for the coating permeable to the passage of the agent, the surface area of the agent that must be coated with the coating impermeable to the passage of the agent may be determined. This is done by progressively reducing the available surface area until the desired release rate is obtained.

Exemplary microporous materials suitable for use as a second coating layer, for instance, are described in U.S. Pat. No. 4,014,335 which is incorporated herein by reference in its entirety. These materials include cross-linked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen. Cross-linked polyvinyl alcohol is preferred. The second coating layer is selected so as to slow release of the agent from the inner core into contact with a mammalian organism, e.g., a human. The second coating layer need not provide gradual release or control of the agent into the biological environment, however, the second coating layer may be advantageously selected to also have that property or feature.

The devices of the present invention may be made in a wide variety of ways, such as by obtaining an effective amount of the agent and compressing the agent to a desired shape. Once shaped, a first coating layer may be applied. In the case of the ethylene vinyl acetate, the first coating layer may be applied directly in the form of a sheet or membrane to the outer surface of the agent. Optionally, the effective agent may have a permeable coating applied to its entire surface prior to coating with the first coating layer. See FIG. 2. Once the first coating layer is applied to the device, the second coating layer may be applied. In the case of polyvinyl alcohol, the second coating may be applied by dipping the device one or more times in a solution containing the desired polymer. Optionally, the second coating layer may be applied by dropping, spraying, brushing or other means of coating the outer surface of the device with the polymer solution. When using a polyvinyl alcohol solution to obtain the second coating layer, the desired thickness may be obtained by applying several coats. Each coat may be dried prior to applying the next coat. Finally, the device may be heated to adjust the permeability of the outer coating.

The above description of how to make the devices of the present invention is merely illustrative and should not be considered as limiting the scope of the invention in any way, as various compositions are well known by those skilled in the art. In particular, the methods of making the device depends on the identity of the active agent and polymers selected. Given the active agent, and the composition of both the first coating and the second coating, one skilled in the art could easily make the devices of the present invention using conventional coating techniques.

The method for treating a mammalian organism to obtain a desired local or systemic physiological or pharmacological effect includes administering the sustained release drug delivery device of the present invention to the mammalian organism and allowing the agent to pass through the device to come in direct contact with the mammalian organism.

The drug delivery system of the present invention may be administered to a mammalian organism via any route of administration known in the art. Such routes of administration include intraocular, oral, subcutaneous, intramuscular, intraperitoneal, intranasal, dermal, and the like. In addition, one or more of the devices may be administered at one time or more than one agent may be included in the inner core.

The drug delivery system of the present invention is particularly suitable for direct implantation into the vitreous of the eye and for application to an intraocular lens.

These methods of administration and technique for their preparation are well known by those of ordinary skill in the art. Techniques for their preparation are set forth in *Remington's Pharmaceutical Sciences*.

The drug delivery system may be administered for a sufficient period of time and under conditions to allow treatment of the disease state of concern.

For localized drug delivery, the devices may be surgically implanted at or near the site of action. This is the case for devices of the present invention used in treating ocular conditions, primary tumors, rheumatic and arthritic conditions, and chronic pain.

For systemic relief, the devices may be implanted subcutaneously, intramuscularly or intraperitoneally. This is the case when devices are to give sustained systemic levels and avoid premature metabolism. In addition, such devices may be administered orally.

In one embodiment of the invention, an ocular device containing ganciclovir as the effective agent in an effective amount to prevent a virus from replicating may be prepared. As further shown in the Examples which follow, such devices may be used to effectively combat and inhibit reproduction of cytomegalovirus retinitis, when surgically implanted into the vitreous of the eye. Such devices may remain in the vitreous permanently after treatment is complete. The preferred amount of ganciclovir used in these devices ranges from about 0.01 mg to about 20 mg. More preferably, such devices contain from about 2 mg to about 10 mg of ganciclovir. These preferred ranges may provide sustained release of the ganciclovir for a period of from several hours to over one year. The preferred first coating layer is ethylene vinyl acetate. The preferred second coating layer is polyvinyl alcohol. When such devices are prepared for implantation within the vitreous of the eye, it is preferred that the device does not exceed about 5 millimeters in any direction. Thus, the cylindrical device shown in FIG. 2 would preferably not exceed 5 millimeters in height or diameter. In addition, the preferred thickness of the first coating layer ranges from about 0.1 to about 1.0 millimeters. The preferred thickness of the second coating layer ranges from about 0.1 to about 2.0 millimeters.

In another embodiment of the invention, an ocular device containing 5-FU as the effective agent may be prepared. As further shown in the Examples which follow, such devices may be used to effectively maintain the intraocular pressure of glaucoma patients after filter surgery when implanted under the conjunctiva of the eye. The preferred amount of ganciclovir used in these devices ranges from about 0.01 mg to about 20 mg. More preferably, such devices contain from about 2 mg to about 15 mg. These preferred ranges may provide sustained release of the 5-FU for a period of from several hours to over 2 months. Preferred materials include ethylene vinyl acetate as the first coating layer and polyvinyl alcohol as the second coating layer. The preferred thickness of the first coating layer ranges from about 0.01 to about 1.0 millimeters. The preferred thickness of the second coating layer ranges from about 0.01 to about 2.0 millimeters.

Optionally, one or more of the devices could be attached to an intraocular lens or the haptic extending therefrom. Intraocular lenses having the devices of the present invention attached thereto and containing 5-FU, colchicine or dexamethasone are particularly suitable for treating patients that have undergone extra capsular cataract surgery. Specifically, such devices may be used to reduce proliferation of remnant lens cells thus preventing or reducing posterior capsular opacification.

While the above described embodiments of the invention are described in terms of preferred ranges of the amount of effective agent, and preferred thicknesses of the preferred first and second coating, these preferences are by no means meant to limit the invention. As would be readily understood by one skilled in the art, the preferred amounts, materials and dimensions depend on the method of administration, the effective agent used, the polymers used, the desired release rate and the like. Likewise, actual release rates and release duration depend on a variety of factors in addition to the above such as the disease state being treated, the age and condition of the patient, the route of administration as well as other factors which would be readily apparent to those skilled in the art.

The following examples are merely illustrative of the present invention and they should not be considered as limiting the scope of the invention in any way, as these examples and other equivalents thereof will become more apparent to those skilled in the art in light of the present disclosure.

EXAMPLE 1

Intraocular Sustained Release of Antiviral Agents

This example demonstrates that the severe problems associated with present GCV therapy may be avoidable by delivering the drug locally thus avoiding high systemic drug levels. The present inventors have developed an implantable device that will release GCV within the eye for over 90 days. The device is composed of 6 mg GCV encased in layers of ethylene vinyl acetate (EVA) and polyvinyl alcohol (PVA).

Characteristics of Polymers

EVA membranes were prepared by compressing EVA at 180° C. under 5 tons of pressure. PVC membranes were prepared from solutions of PVA which were dried to a film and then heated to 125, 150 or 180° C. The permeability of EVA and PVA membranes to GCV was measured in vitro using parallel glass diffusion chambers (Crown Glass Co., Somerville, N.J.). One ml solutions of GCV were prepared in normal phosphate buffer (pH 7.4) and applied to the donor side of the chambers. The permeation of GCV across the membranes to the receptor compartment was measured for 3 hours at 37° C. The devices were found to release GCV in a linear manner for approximately 120 days in vitro with a mean release rate of approximately 50 µg/day.

Preparation and Testing of the Devices 6 mg pellets of GCV were prepared by direct compression using a 2.5 mm die. These were surrounded on three sides with the impermeable EVA membrane and then coated in a 10% PVA solution. After being allowed to dry for 24 hours, the device was cured at 180° C. for 4.7 hours to further reduce the release rate. The release rate of GCV from the devices prepared above was measured in vitro by immersing each device in 5 ml of isotonic phosphate buffer (pH 7.4). One ml samples were periodically withdrawn and replaced with fresh buffer and the buffer solution was changed every 10 days to avoid microbial growth.

The apparent permeability coefficient of GCV across PVA membranes was dependent on the temperature which they had been treated. The change in physical properties of the membranes is due to alterations in crystal structure of polymer. The permeability of GCV across EVA membranes was too low for permeability coefficients to be calculated. The permeability of GCV across PVA membranes is set forth in Table 1 below.

TABLE 1

| PERMEABILITY OF GCV ACROSS PVA MEMBRANE TREATED AT VARIOUS TEMPERATURES | |
|---|---|
| Membrane Treatment (°C.) | Papp (cm/s × $10^{-7}$) +/− SD, N = 4 |
| 125 | 8.3 +/− 0.6 |
| 150 | 2.1 +/− 0.2 |
| 180 | 0.9 +/− 0.1 |

In Vivo Testing of Devices

Devices were surgically implanted into both the subconjunctival space and the vitreous of albino rabbits. After 10 days, the animals were sacrificed and a histological examination was performed. In another group of animals, devices were implanted into the posterior chamber of the eye and samples of vitreous humour was periodically removed. In a third group of animals devices were implanted into the vitreous of both eyes. The animals were killed 10, 30, 40, 70 and 80 days after implantation of the devices. The devices and vitreous samples removed for analysis. The concentration of GCV in these samples was determined by HPLC with UV detection at 254 nm. A C-18 reverse phase column was used with mobile phase of 0.02% ammonium acetate buffer (pH 4.0) and a flow rate of 1 ml/min. The effect of implantation on retinal function was assessed by performing electroretinogram (ERG) examinations before and after the study.

Histologic examination gave no indication of toxicity or inflammatory reaction due to the implantation of the device. Some inflammation was noted around the suture used to hold the device in place suggesting that this produced a worse reaction than the device itself. Analysis of vitreal samples showed that the device maintained GCV levels in the vitreous at or above 2 µg/ml for over 80 days. The ERG data suggests that the levels of GCV obtained cause no retinal toxicity in the rabbit eye. The possibility exists for drug resistance to develop in CMV although there have been no reports of this as yet. Resistance to GCV, should it occur, could be countered by the use of other drugs (Foscarnet or trifluorothymidine) in similar release devices.

CONCLUSION

The implantation of controlled release devices for the release of GCV appears to offer some significant advantages over existing therapy. The work performed in rabbits indicates that vitreal concentrations of GCV can be maintained above the ID 100 for CMV for a prolonged period without high systemic exposure. This will, if effective, treat potentially blinding CMV retinitis and allow concurrent therapy of AZT for HIV. It is anticipated that fewer complications will arise from this procedure than occur in repeated intravitreal injections.

EXAMPLE 2

Intravitreal Sustained Release of Ganciclovir: Membrane Permeability and Device Construction The following paragraphs illustrate the membrane permeability and device construction of particular embodiments of the present invention.

Ganciclovir was obtained from Syntex Laboratories as a free acid in powdered form. Alternatively, the free acid of ganciclovir was prepared by neutralizing an aqueous solution of the commercially available salt (pH 11.2). The precipitated product was then purified with two successive recrystallizations from 95% ethanol. The buffer solution was composed of sodium bicarbonate (0.68%), potassium bicarbonate (0.03%), and sodium chloride (0.65%), in distilled water. The pH of the buffer solution was adjusted to 7.4 prior to use. Polyvinyl alcohol (PVA) of 76–78,000 M.W. and 98% hydration was obtained from Aldrich Chemical Co. Ethylene vinyl acetate was obtained from Du Pont of Wilmington (trade name ELVAX, grade 40w).

Diffusion Cell Studies

PVA membranes were prepared by dissolving 4 grams of PVA in 200 ml of distilled water at 60° C. The PVA solution was allowed to cool to 22° C. and the entire mixture was poured so that it completely covered a silicanized glass slab measuring 35 cm by 46 cm. After drying for 16 hours, the PVA film was removed from the slab. Membranes prepared in this fashion were then heat cured in a convection oven for 4 hours at 190° C.

Diffusion cell studies were performed by placing the membranes between the compartments of a glass diffusion cell (Crown Glass Co., Somerville, N.J.). The internal diameter of these cells was 1 cm (total surface area of diffusion 0.78 $cm^2$); the volume of each compartment was 3 ml. Small magnetic stirring rods were placed in each compartment and operated by a magnetic stirring unit. The entire assembly was maintained at 37° C by a circulating water bath. Membranes were first soaked in isotonic buffered saline (pH 7.4) for 30 minutes and then loaded into the chambers. With the membrane in place, buffer solution was added to each compartment and left in place for 30 minutes to allow for hydration of the membrane and then removed. A 0.025% solution of GCV in isotonic buffered saline was added to the donor compartment and the buffer solution was added to the receptor compartment. The contents of the receptor compartment were periodically removed for analysis and replaced with fresh buffer solution thus maintaining sink conditions.

An ultraviolet spectrophotometry assay was used to determine concentrations of ganciclovir (252 nm, detection limit 0.1 $\mu$g/cc). A linear relationship between absorbance and concentration was demonstrated using known concentrations of drug in a tear buffer solution.

Sheets of EVA membrane were prepared by compressing 3.5 gm pellets under 4 metric tons at 190° C to a thickness of 0.6 mm. Diffusion cell studies were performed with EVA membranes as described above for PVA. It was found that GCV did not permeate through the EVA layer.

Device Construction

Because EVA was found to be impermeable to ganciclovir it was used in these devices as a blocking agent. EVA membranes were prepared as described above. A six milligram pellet of GCV was compressed under 500 pounds of pressure into pellets measuring 2.5 mm in diameter.

A first type of sustained release GCV device releasing 2 $\mu$g/hr was prepared by coating the 6 mg pellet of ganciclovir in 300 $\mu$l of a 10% PVA solution and allowing the coated pellet to dry. The pellet was then coated on three sides with a film of prepressed EVA and capped by a 3 mm disc of EVA coated in 10% PVA. The pellet was thus completely surrounded by EVA apart from a thin ring of PVA between the EVA walls and the cap. See FIG. 2. The assembly was then completely coated in 10% PVA and allowed to dry overnight. The embedded pellet was cut out in a disc shape using a 4 mm punch. A suturing strut was attached to the device by bonding a strip of dry 10% PVA to the bottom of the device with a drop of 2% PVA. The device was subsequently baked at 190° C for 4.75 hours.

A second type of device releasing 5 $\mu$g/hr was prepared in the same manner except that GCV pellets had only the top and bottom surfaces covered with EVA.

Release Rate Studies

The devices were placed in 10 ml of isotonic buffered saline at 37° C. This solution was periodically sampled and changed to maintain sink conditions. The concentration of GCV in these samples was determined by HPLC with UV detection at 254 nm absorbance. Absorbance values of the samples were converted to drug concentrations and cumulative drug release (average of three trials) was plotted against time.

As stated above, the GCV devices released ganciclovir at a rate of 2±0.5 $\mu$g/hr (first type) and 5±1 $\mu$g/hr (second type).

Device/Drug Stability

Near IR of the individual components (EVA, PVA and ganciclovir) showed no change after heat treatment; however, the device showed a single new peak at approximately 2075 nm. In addition, there was no apparent drug loss or decomposition after heat treatment of the ganciclovir pellet based on HPLC analysis, and a scanning EM of the device demonstrated that there were no holes or cracks in the walls of the device after heat treatment.

EXAMPLE 3

Intravitreal Sustained Release of Ganciclovir: In Vivo Pharmacokinetics and Tolerability The membrane permeability studies, the construction of the implants and the in vitro release rate studies of the implants used in this study are described in Example 2. Implants releasing 2 or 5 $\mu$g/hr in vitro were prepared. Implants were sterilized with ethylene oxide gas by the Sterile Products Division of the Veterans Administration Hospital in Lexington, Ky. Quality control was ensured by measuring the in vitro release rate of every fifth device. Sterility was ensured by sending every fifth device for culture.

New Zealand albino rabbits weighing 1.5 to 2 kg were used in this study. Anesthesia was provided with intramuscular ketamine HCl (40 mg/kg), attopine sulfate (0.1 mg/kg), xylazine HCl (10 mg/kg) and topical proparacaine (0.5%). Pupillary dilation was achieved with topical phenylephrine (2.5%) and tropicamide (1%) drops.

A baseline photopic electroretinogram (ERG) was recorded preoperatively in each rabbit using a corneal contact lens. A Gansfeld stimulus was used to improve standardization of results. After sedation, the rabbits were placed inside a Gansfeld stimulator 20 cm away from the flash unit. Flash (cone and rod response) and flicker (cone response) ERGs were done under light adapted conditions. Graphic measurements were recorded, and the waveform amplitudes and implicit times were calculated.

Cryopexy was then applied to the superior 180 degrees of the peripheral retina in each eye to decrease the chance of retinal detachment related to EVA/PVA membrane insertion or vitreous sampling. This was done because the pars plana of the New Zealand albino rabbit is poorly developed and it was therefore necessary to implant the devices and take vitreous samples through retina. The ERG was repeated four weeks later immediately prior to insertion of the device.

All intraocular procedures were done under sterile conditions and conformed to the ARVO specifications for the ethical treatment of experimental animals. After placement of a lid speculum, a 360 degree conjunctival peritomy was performed. The rectus muscles were secured with 2-0 black silk suture. Using indirect ophthalmoscopy, the area of previous cryopexy was localized and marked with scleral diathermy.

The EVA/PVA device was immersed in sterile saline prior to placement of a 7-0 silk suture through the external PVA supporting tag. A MVR blade was used to create a 5 mm sclerotomy site through the area cryopexy. Penetration into the vitreous was verified by direct visualization of the MVR blade through the dilated pupil. The device was placed into the vitreous cavity and secured to the sclera with the 7-0 silk suture that was attached to the external PVA supporting tag. Remaining defects in the sclera were closed with 7-0 silk in an interrupted fashion. Topical antibiotic drops consisting of polymyxin B, bacitracin, and neomycin were instilled into each eye twice daily for three days after each procedure.

In a first group of nine rabbits, the right eye was treated with a device without GCV (control eyes), while the left eye was given a device containing 6 mg of GCV releasing at $5\pm1$ μg/hr (treatment eyes). Vitreous samples were periodically removed using a 20 gauge needle on a tuberculin syringe. Entrance into the vitreous cavity was verified by observation of the needle through the dilated pupil. Retinal examination with indirect ophthalmoscope was performed on each eye prior to each vitreous sampling. After removal, vitreous samples were stored at $-60°$ C until analyzed by HPLC. ERG's were repeated one and two months after device implantation.

After the last ERG, the rabbits were sacrificed with an overdose of intravenous sodium pentobarbital. At this time, no GCV was detectable in the vitreous. Enucleated eyes were fixed in 70% formaldehyde-glutaraldehyde solution, dehydrated in alcohol, embedded in paraffin, and sectioned with microtome. Tissues were stained with hematoxylin-eosin and examined under a light microscope.

In a second group of 10 rabbits, a device containing 6 mg of GCV releasing at $2\pm0.5$ μg/hr was implanted into both eyes. Vitreous samples were not collected from the treated eyes. Instead, the rabbits were sacrificed 10, 30, 40, 70 and 80 days after implantation. As with the first group, retinal examination was performed with an indirect ophthalmoscope and ERGs were performed immediately prior to sacrifice. In this group, devices were removed from the eyes and the amount of GCV still present determined by HPLC.

The animals were killed with an overdose of intravenous sodium pentobarbital when no detectable GCV was present in the treatment eyes. Enucleated eyes were fixed in 20% formaldehyde-glutaraldehyde solution, dehydrated in alcohol, embedded in paraffin, and sectioned with a microtome. Tissues were stained with hematoxylin-eosin and examined by light microscopy.

In the final experimentation group, 6 mg of GCV was placed into the vitreous of one rabbit (both eyes) through the pars plana to assess retinal toxicity in the "worst case scenario" event of immediate device breakdown. ERGs were done preoperatively and on postoperative days 2, 11, and 48.

Results

In this investigation, mean GCV vitreous concentrations in the first group ranged from 14 μg/ml to 19 μg/ml for 42 to 56 days after EVA/PVA device insertion. The calculated mean in vivo release rate was approximately 5 μg/hr. No detectable drug was measured 72 days after device implantation in any eye from the first group. In the second group, GCV was present in the vitreous at over 2 μg/ml for over 80 days. Implanted devices were found to have released GCV at approximately 2 μg/hr in vivo. This would suggest that levels would be maintained in the vitreous for approximately 120 days.

The device was well tolerated in both groups demonstrating no evidence of intraocular inflammation by indirect ophthalmoscopy. Five treatment eyes from the first group developed lens opacification (5/9, 56%). None of the eyes from the control group or eyes from the second group developed lens opacification (0/19, 0%). Two of the 5 eyes that developed lens opacification developed a dim use white cataract after direct trauma to the lens during vitreous sampling. The other eyes that developed lens opacification developed a focal, nonprogressive lens opacity also believed to be related to vitreous sampling. No cataract formation occurred in any of the eyes in which a device containing ganciclovir was placed and no vitreous sampling was performed.

Retinal detachment occurred in two treatment eyes (2/9, 22%) from group one and in none of the eyes from the control group or the eyes from the second group (0/19, 0%). Both retinal detachments were thought to be related to traumatic vitreous sampling and not a secondary response to the device.

No detachments or other abnormalities occurred in the second group of animals which were not periodically sampled.

Flash (rod and cone response) and flicker (cone response) ERG measurements were obtained preoperatively and postoperatively in all eyes. No significant deterioration of the flash or flicker ERG wave amplitudes occurred in either group one or two eyes. No significant prolongation of the ERG implicit times occurred in either group. Modest abnormalities seen in the postoperative ERG b-wave amplitudes and implicit times were most likely related to the cryopexy.

Histological examination of the retina showed no significant difference between the control and treatment eyes. Light microscopic examination of both groups revealed normal retinal architecture.

The two eyes from the final group that received a 6 mg bolus dose of intravitreal GCV showed no evidence of toxicity by indirect ophthalmoscopy. Postoperatively, the photopic flash ERG remained unchanged throughout, while the photopic flicker ERG showed a 50% deterioration in b-wave amplitude and modest delay in implicit time beginning 48 hours after GCV administration. The flicker ERG completely recovered in one eye and partially in the other 48 days after GCV administration.

No observable retinal toxicity was present by ERG or light microscopic examination of retinal tissue postoperatively. Chronic low concentrations of GCV appear to be well tolerated by the retina. Although some ERG changes were noted with the implantation of 6 mg of uncoated GCV it does not appear that complete device breakdown would result in permanent retinal damage. We believe that the cataracts which formed in the 5 eyes of group one were secondary to lens trauma from the repeated vitreous taps rather than drug toxicity. No lens opacification occurred in either the eyes from the control group or the eyes from the second group in which frequent vitreous taps were not performed.

The device was easily inserted through the area of cryopexy in the rabbit. Applicants believe that the retinal detachments seen in two treatment eyes of the first group were a reflection of the difficulty working with rabbit eyes (poorly formed pars plana, low scleral rigidity, and large lens) rather than complications due to the drug or device itself. No detachments occurred in the eyes from the control group or the eyes from the second group that were not undergoing frequent vitreous taps.

There was minimal inflammatory response to the EVA/PVA device alone. These polymers are biologically inert and are well tolerated by the eye. This is a non-biodegradable system. Although this may be considered a drawback, the reliable release rates over extended periods of time and the lack of inflammatory response would be very difficult to obtain using an erodible drug delivery system. Our in vitro release rates seem to be predictive of the in vivo release rate. In the eyes from the second group, drug devices were constructed to release GCV at a slower rate to extend the duration of treatment. Increasing the amount of drug carried in the device would also be technically simple and could extend the duration of GCV release to the vitreous for several months.

EXAMPLE 4

Intravitreal Sustained Release of Ganciclovir In Vivo Pharmacokinetics and Tolerability: Human Studies The membrane permeability studies, the construction of the implants and the in vitro release rates studies of the implants used in this study are described in Example 2. The devices used were those which released GCV at 2 $\mu$g/hr.

Eight humans infected with AIDS were used in this study. One eye of each patient treated with an implant containing ganciclovir. The implant was surgically positioned within the vitreous. The other eye of each patient was used as a control, that is, was not treated with ganciclovir. In all eight patients, vision stabilized in the eye treated with the implant. See Table 2 below. In Table 2, the first column indicates the initials of the patient. The second column indicates the visual acuity of the patient prior to implantation. The third column indicates the visual acuity of the patient on the last day, the vision of the patient was checked before death.

TABLE 2

| PATIENT | Vision of Patients Treated With Implant | | |
|---|---|---|---|
| | BEFORE | AFTER | DAYS |
| SFR | 20/70 | 20/70 | 21 |
| ELM | 20/20 | 20/25 | 28 |
| KRS[1] | CF[2] | CF[2] | 24 |
| RM | 20/80 | 20/80 | 19 |
| BR | 20/20 | 20/40 | 26 |
| CMP | 20/30 | 20/30 | 9 |
| CRW | 20/40 | 20/40 | 7 |
| EL | 20/20 | 20/40 | 50 |

Figure 4:
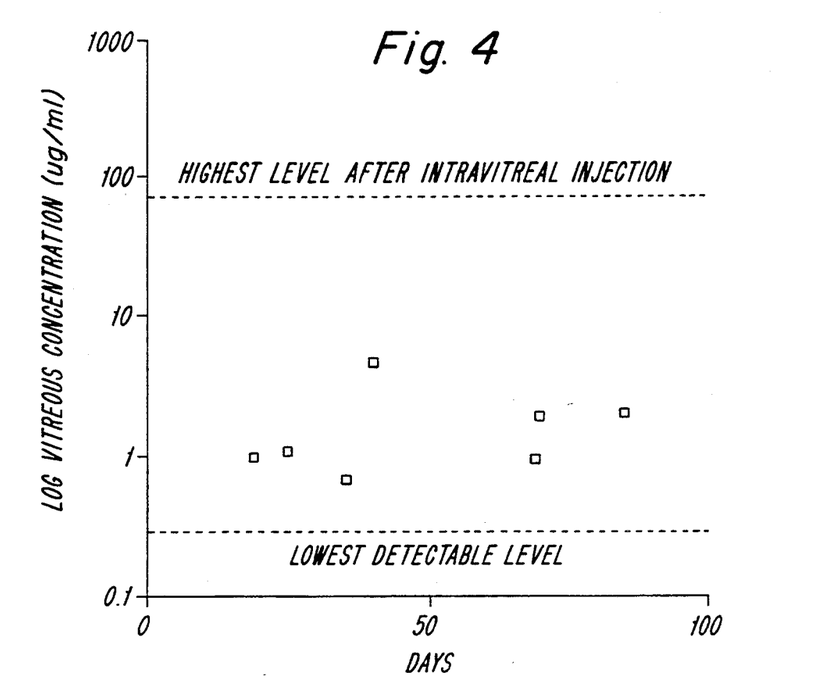
FIG. 4 is a graph showing the concentration of ganciclovir found in humans and delivered by an ocular device of the present invention over time.
Figure 5:
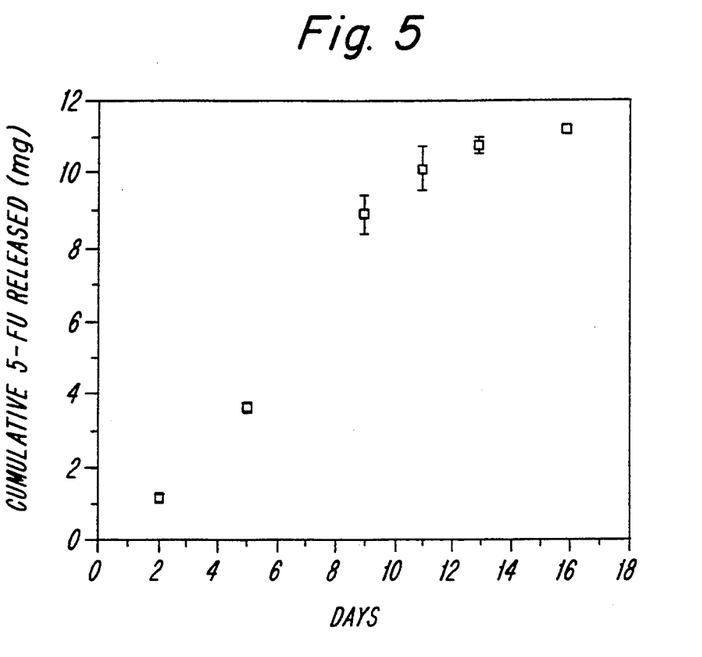
FIG. 5 is a graph showing the concentration of 5-fluorouracil (5-FU) delivered by devices of the present invention over time.

[1]Retina was detached at time of implantation but was repaired during implantation. Subsequently, the retina redetached.
[2]Count Fingers Vision Failure In addition, progression of the disease arrested or reversed in the eye treated with ganciclovir. Table 3 below and the photography in FIG. 5 show the progression of the disease. FIG. 4 shows the concentration of GCV over time.

TABLE 3

| PATIENT | Progression of CMV in Patients Treated with Implant | |
|---|---|---|
| | TREATED EYE | CONTROL EYE |
| SFR | stable | progressed |
| ELM | improved | progressed |
| KRS | progressed | progressed |
| RM | improved | no disease |
| BR | improved | no disease |
| CMP | stable | progressed |
| CRW | improved | no disease |
| EL | improved | progressed |

Visual activity was determined by a standard eye exam and disease progression by fundus photograph.

Samples of vitreous from human eyes were analyzed by high performance liquid chromatography (HPLC) using a C-18 reverse phase column with a 0.02% ammonium acetate mobile phase (pH 4.0). Under these conditions, GCV has a retention time of 31 minutes. This work has shown that implantation of the devices maintains GCV levels of approximately 1.5 $\mu$g/ml in the vitreous for over 70 days.

EXAMPLE 5

Sustained Release of 5-FU Using a Heat Treated Membrane System of Layered Ethylene Vinyl Acetate and Polyvinyl Alcohol In Vitro Studies Subconjunctival administration of 5-FU as an adjunct to filtration surgery in high risk glaucoma patients is attended by the necessity of multiple subconjunctival injections and the potentially serious complications due to delayed wound healing. Alternative delivery systems have been proposed including liposomes, topical administration, and sustained release polymers. Work with diffusion of 5-FU through ethylene vinyl acetate (EVA) and polyvinyl alcohol (PVA) membranes showed that EVA was impermeable to 5-FU while PVA provided a linear release that appeared to be optimal for the sustained release of 5-FU (J. Ocular Pharmacol. 1988;1062:231). Applicants found that release rates could be markedly decreased by heat treating the PVA membrane. Nonetheless, Applicants found that an improved system could be made by optimizing the release rate using a layered EVA/PVA system. Therefore, the rate of release was further decreased by layering EVA within the PVA to create a membrane system that was 6×8 mm in size.

Device Construction

A 6 milligram pellet of 5-FU was compressed under 500 pounds of pressure into pellets measuring 2.5 mm in diameter. Sustained release 5-FU devices were prepared by coating the 6 mg pellet of 5-FU in 300 $\mu$l of a 10% PVA solution and allowed to dry. The pellet was then coated on three sides with a film of prepressed EVA and capped by a 3 mm disc of EVA coated in 10% PVA. The pellet was thus completely surrounded by EVA apart from a thin ring of PVA between the EVA walls and the cap. See FIG. 2. The assembly was then completely coated in 10% PVA and allowed to dry overnight. The embedded pellet was cut out in a disc shape using a 3.5 mm punch. A suturing strut was attached to the device by bonding a strip of dry 10% PVA to the bottom of the device with a drop of 2% PVA. The device was subsequently baked at 190° C for three hours. With this design, Applicants were able to decrease the release rate to approximately 4 μg/hr (4.16±0.43 μg/hr, n=3) and to sustain the release over one month in vitro.

In Vivo Studies

The above-described devices were implanted subconjunctivally in four rabbits to study possible in vivo toxicity from the device and 5-FU.

Devices containing 6 mg of 5-FU were implanted on the exposed sclera 1.0 mm from the limbus superiorly in the right eye of four rabbits under general anesthesia. The left eye was undisturbed and used as a control.

ERG's and fundus photographs done prior to sacrificing showed no retinal toxicity from the device or the 5-FU. Intraocular pressure measurements showed no significant difference between the eyes. Histology on the implanted eye showed no inflammation related to the device or other histologic abnormality. Devices retrieved after sacrificing were found to have no drug remaining in them. We have shown that our system for sustained release is biologically inert and releases 5-FU at a rate that does not achieve toxic level. We feel this method of delivery has great promise in the therapy of the glaucoma patient at risk for failure of filtration surgery.

EXAMPLE 6

Sustained Release of 5-FU Using a Heat Treated Membrane System of Layered Ethylene Vinylacetate and Polyvinyl Alcohol

Device Construction

A twelve milligram pellet of 5-FU was compressed under 500 pounds of pressure into pellets measuring 2.5 mm in diameter. Sustained release 5-FU devices were prepared by coating the 12 mg pellet as described in Example 5.

Release Rate Studies

The devices were placed in 10 ml of isotonic buffered saline at 37° C. The solution was periodically sampled and changed to maintain sink conditions. The concentration of GCV in these samples was determined by HPLC with UV detection at 254 nm absorbance. Absorbance values of the samples were converted to drug concentrations and cumulative drug release (average of three trials) was plotted against time. See FIG. 5.

In Vivo Studies

Implants prepared as described above were surgically implanted in the eyes of monkeys which have undergone filtering surgery. Intraocular pressure (IOP) tends to increase in monkeys which have undergone filtering surgery. Thus, the aim of this study was to maintain low IOP in monkeys after filtering surgery by the use of a sustained release 5-FU. In one eye of each monkey, a device containing 12 mg of 5-FU was implanted under the conjunctiva after surgery. In the other eye of each monkey, a device containing no 5-FU was implanted under the conjunctiva after surgery.

Figure 6:
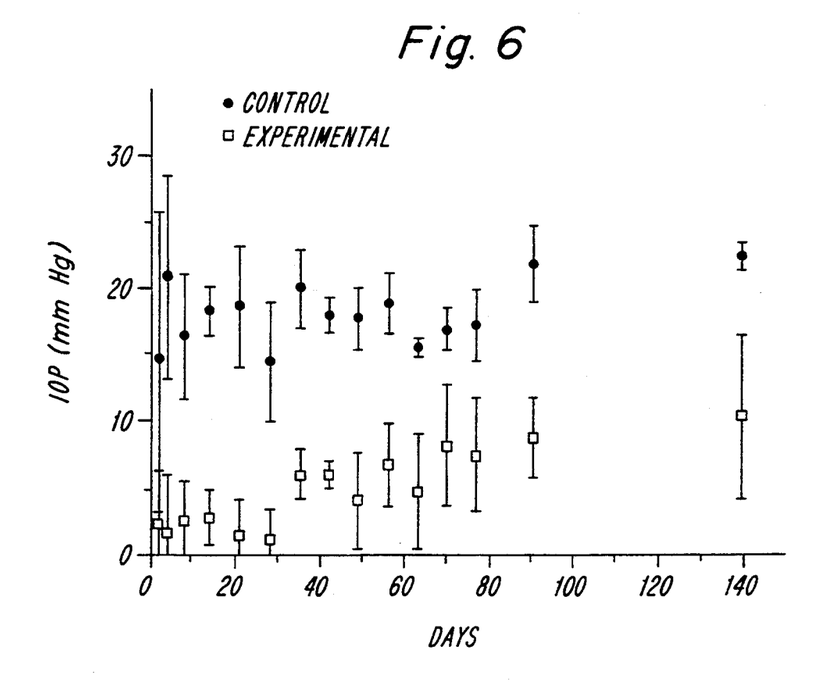
FIG. 6 illustrates the intraocular pressure of monkeys over time, wherein under the conjunctiva of one eye of each monkey was implanted a device of the present invention.

FIG. 6 illustrates the intraocular pressure of a mean average of three monkeys versus time in days. As clearly illustrated, the treated eyes maintained an intraocular pressure below that of the untreated (control) eyes.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

We claim:

1. A method for treating a mammalian organism to obtain a desired local or systemic physiological or pharmacological effect comprising:
   administering a sustained release drug delivery system to a mammalian organism in need of such treatment, said drug delivery system comprising;
   (1) an inner core or reservoir comprising an effective amount of an agent to obtain a desired local or systemic physiological or pharmacological effect,
   (2) a first polymer coating layer, said first coating layer essentially impermeable to the passage of said agent, and said first polymer coating layer covering at least a portion of the inner core, wherein at least a small portion of the inner core is not coated with said first coating layer, and
   (3) a second polymer coating layer permeable to the passage of said agent, wherein said second polymer coating layer essentially completely covers said first polymer coating layer and the uncoated portion of the inner core, whereby said agent is able to pass through said second polymer coating layer in a controlled manner wherein said first polymer coating layer and said second polymer coating layer are essentially insoluble and inert in body fluids.

2. A method for treating a mammalian organism as claimed in claim 1, wherein said second coating layer comprises polyvinyl alcohol.

3. A method for treating a mammalian organism as claimed in claim 2, wherein said first coating layer comprises ethylene vinyl acetate.

4. A method for treating a mammalian organism as claimed in claim 3, wherein said effective agent comprises 5-fluorouracil or ganciclovir.

5. A method for treating a mammalian organism for cytomegalovirus retinitis comprising:
   administering a sustained release drug delivery system to a mammalian organism in need of such treatment, said drug delivery system comprising;
   (1) an inner core or reservoir comprising an effective amount of ganciclovir effective to obtain a desired local or systemic physiological or pharmacological effect,
   (2) a first polymer coating layer, said first polymer coating layer essentially impermeable to the passage of said ganciclovir, and said first polymer coating layer covering at least a portion of the inner core, wherein at least a small portion of the inner core is not coated with said first polymer coating layer, and
   (3) a second polymer coating layer permeable to the passage of said ganciclovir, wherein said second polymer coating layer essentially completely covers said first polymer coating layer and the uncoated portion of the inner core, whereby said ganciclovir is able to pass through said second polymer coating layer in a controlled manner.

6. A method for treating a mammalian organism to obtain a desired physiological or pharmacological effect comprising:

placing a sustained release drug delivery system in contact with or within an eye of a mammalian organism in need of such treatment, said drug delivery system comprising;

(1) an inner core having an effective amount of an agent to obtain a desired local or systemic physiological or pharmacological effect and an inner polymer coating permeable to the passage of said agent covering at least a portion of said agent, (2) a first polymer coating essentially impermeable to the passage of said agent, said first polymer coating covering at least a portion but not the entire surface area of said inner polymer coating of said inner core, and (3) a second polymer coating permeable to the passage of said agent, wherein said second polymer coating essentially completely covers said first polymer coating and any uncoated portion of the inner core, whereby said agent is able to pass through said second polymer coating, wherein each of the polymers selected to make the device are essentially insoluble and inert in body fluids and compatible with eye tissues, and allowing said agent to pass through said second polymer coating to obtain a desired effect.

7. The method for treating a mammalian organism according to claim 6, wherein said inner coating of said inner core comprises polyvinyl alcohol.

8. The method for treating a mammalian organism according to claim 6, wherein said first coating comprises ethylene vinyl acetate.

9. The method for treating a mammalian organism according to claim 6, wherein said second coating comprises polyvinyl alcohol.

10. The method for treating a mammalian organism according to claim 6, wherein said agent is ganciclovir or 5-fluorouracil.

11. The method for treating a mammalian organism according to claim 6, wherein said inner coating of said inner core comprises polyvinyl alcohol, said first coating comprises ethylene vinyl acetate, said second coating comprises polyvinyl alcohol and said agent is cyclosporin, dexamethasone, 5-fluorouracil or ganciclovir.

12. A sustained release drug delivery system suitable for placing in contact with or within the eye to provide a desired physiological or pharmacological effect comprising:

(1) an inner core having an effective amount of an agent to obtain a desired local or systemic physiological or pharmacological effect and an inner polymer coating permeable to the passage of said agent covering at least a portion of said agent, (2) a first polymer coating essentially impermeable to the passage of said agent, said first polymer coating covering at least a portion but not the entire surface area of said inner polymer coating of said inner core, and (3) a second polymer coating permeable to the passage of said agent, wherein said second polymer coating essentially completely covers said first polymer coating and any uncoated portion of the inner core, wherein each of the polymers selected to make the device are essentially insoluble and inert in body fluids and compatible with eye tissues.

13. The sustained release drug delivery system suitable for placing in the eye according to claim 12, wherein said inner coating of said inner core comprises polyvinyl alcohol.

14. The sustained release drug delivery system suitable for placing in the eye according to claim 12, wherein said first coating comprises ethylene vinyl acetate.

15. The sustained release drug delivery system suitable for placing in the eye according to claim 12, wherein said second coating comprises polyvinyl alcohol.

16. A method for providing controlled and sustained administration of an agent effective in obtaining a desired local or systemic physiological or pharmacological effect comprising:

surgically implanting a sustained release drug delivery system at a desired location, said drug delivery system comprising;

(1) an inner core or reservoir comprising an effective amount of an agent effective in obtaining a desired physiological or pharmacological effect, (2) a polymer coating layer which is essentially impermeable to the passage of said effective $\mu$gent, said impermeable layer covering at least a portion or the inner core, wherein at least a small portion of the inner core is not coated with said impermeable polymer coating layer, and (3) a polymer coating layer which essentially completely covers the inner core and is permeable to the passage of said effective agent whereby said agent is able to pass through said polymer coating layer in a controlled manner.

17. A method as claimed in claim 16, wherein said device is surgically implanted within the vitreous of the eye.

18. The sustained release drug delivery system suitable for placing in the eye according to claim 12, wherein said agent is cyclosporin, dexamethasone, 5-fluorouracil or ganciclovir.

19. A method as claimed in claim 17, wherein said permeable coating layer comprises polyvinyl alcohol.

20. A method as claimed in claim 18, wherein said impermeable coating layer comprises ethylene vinyl acetate.

21. A method as claimed in claim 20, wherein said effective agent is ganciclovir or 5-fluorouracil.

22. A sustained release drug delivery system comprising:

(A) an inner core or reservoir comprising an effective amount of an agent effective in obtaining a desired local or systemic physiological or pharmacological effect, (B) a first polymer coating layer, said first polymer coating layer impermeable to the passage of said effective agent, and said first polymer coating layer covering at least a portion of the inner core, wherein at least a small portion of the inner core is not coated with said first polymer coating layer, and (C) a second polymer coating layer, said second polymer coating layer permeable to the passage of said effective agent, wherein said second polymer coating layer essentially completely covers the first polymer coating layer and the uncovered portion of the inner core, said first polymer coating layer and said second polymer coating layer being essentially insoluble and inert in body fluids.

23. A sustained release drug delivery system as claimed in claim 22, wherein said second coating layer comprises polyvinyl alcohol.

24. A sustained release drug delivery system as claimed in claim 23, wherein said first coating layer comprises ethylene vinyl acetate.

25. A sustained release drug delivery system as claimed in claim 24, wherein said effective agent is ganciclovir or 5-fluorouracil.

26. The method for treating a mammalian organism as claimed in claim 1, wherein said drug delivery system is attached to an intraocular lens or the haptic extending from said intraocular lens.

27. The sustained release drug delivery system suitable for placing in the eye according to claim 12, wherein said inner coating of said inner core comprises polyvinyl alcohol, said first coating comprises ethylene vinyl acetate, said second coating comprises polyvinyl alcohol and said agent is ganciclovir or 5-fluorouracil.

28. The sustained release drug delivery system according to claim 22, further comprising a polymeric layer between said inner core or reservoir and said impermeable coating, whereby said agent is able to pass through said polymeric layer 29. A sustained release drug delivery system comprising:
(a) in inner core or reservoir comprising an effective amount of an agent effective in obtaining a desired local or systemic physiological or pharmacological effect,
(b) a first polymer coating layer, said first polymer coating layer impermeable to the passage of said effective agent, and said first polymer coating layer covering at least a portion of the inner core, wherein at least a small portion of the inner core is not coated with said first polymer coating layer, and
(c) a second polymer coating layer, said second polymer coating layer permeable to the passage of said effective agent, wherein said second polymer coating layer essentially completely covers the first polymer coating layer and the uncovered portion of the inner core, wherein said sustained drug delivery system is attached to an intraocular lens or the haptic extending from said intraocular lens.

30. The sustained drug release delivery system as claimed in claim 29, wherein said effective agent is ganciclovir, 5-fluorouracil, colchicine or dexamethasone.

31. The method for treating a mammalian organism according to claim 1, wherein said sustained release drug delivery system is placed in contact with or within an eye of said mammalian organism.

32. The method for treating a mammalian organism according to claim 1, wherein said sustained release drug delivery system further comprises a polymeric layer between said inner core or reservoir and said impermeable coating, whereby said agent is able to pass through said polymeric layer between said inner core or reservoir and said impermeable coating.

33. The method for treating a mammalian organism according to claim 22, wherein said core consists essentially of said agent or a pharmaceutically acceptable salt of said agent.

34. The method for treating a mammalian organism according to claim 1, wherein said core consists essentially of said agent or a pharmaceutically acceptable salt of said agent.

35. The sustained release drug delivery system according to claim 22, wherein said polymers used to fabricate said first and second layer are compatible with eye tissues. between said inner core or reservoir and said impermeable coating.

* * * * *

UNITED STATES PATENT AND TRADEMARK OFFICE
CERTIFICATE OF CORRECTION

PATENT NO. : 5,378,475
DATED : January 3, 1995
INVENTOR(S) : Thomas J. SMITH et al.

It is certified that error appears in the above-indentified patent and that said Letters Patent is hereby corrected as shown below:

On the title page item [75],
    Inventors:  Thomas J. Smith, Boston, Mass.; Paul Ashton; Paul A. Pearson, both of Lexington, Ky.

Should read as follows:

Inventors:  Thomas J. Smith, Boston, Mass.; Paul Ashton; Paul A. Pearson; David L. Blandford, each of Lexington, KY.

Signed and Sealed this

Fourth Day of April, 1995

Attest:

BRUCE LEHMAN

Attesting Officer    Commissioner of Patents and Trademarks